(12) United States Patent
Woldegebriel et al.

(10) Patent No.: US 12,138,062 B2
(45) Date of Patent: Nov. 12, 2024

(54) DETERMINING WHETHER A HYPOTHESIS CONCERNING A SIGNAL IS TRUE

(71) Applicant: Nokia Technologies Oy, Espoo (FI)

(72) Inventors: Michael Woldegebriel, Espoo (FI); Mikko Honkala, Espoo (FI); Leo Karkkainen, Helsinki (FI); Satu Rajala, Kangasala (FI); Harri Lindholm, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 1080 days.

(21) Appl. No.: 16/770,706

(22) PCT Filed: Dec. 10, 2018

(86) PCT No.: PCT/EP2018/084111
§ 371 (c)(1),
(2) Date: Jun. 8, 2020

(87) PCT Pub. No.: WO2019/115432
PCT Pub. Date: Jun. 20, 2019

(65) Prior Publication Data
US 2021/0161477 A1    Jun. 3, 2021

(30) Foreign Application Priority Data

Dec. 15, 2017    (EP) .................................... 17207764

(51) Int. Cl.
*A61B 5/352*    (2021.01)
*A61B 5/00*    (2006.01)
(Continued)

(52) U.S. Cl.
CPC .............. *A61B 5/352* (2021.01); *A61B 5/353* (2021.01); *A61B 5/355* (2021.01); *A61B 5/358* (2021.01);
(Continued)

(58) Field of Classification Search
CPC ...... G06F 17/18; G06F 17/17; G06F 18/2321; G06F 18/2415; A61B 5/352; A61B 5/353;
(Continued)

(56) References Cited

U.S. PATENT DOCUMENTS

2003/0216654 A1    11/2003    Xu et al. ........................ 600/509
2006/0235319 A1    10/2006    Belohlavek et al. .......... 600/509
(Continued)

OTHER PUBLICATIONS

Li et al., "Probability density distribution of delta RR intervals: a novel method for the detection of atrial fibrillation" Australas Phys Eng Sci Med (2017) (Year: 2017).*
(Continued)

*Primary Examiner* — John C Kuan
(74) *Attorney, Agent, or Firm* — Mccarter & English

(57) ABSTRACT

A method of detection of a recurrent feature of interest within a signal including: obtaining evidence, based on a signal, the evidence including a probability density function for each of a plurality of parameters for parameterizing the signal, including at least one probability density function for a parameter, of the plurality of parameters, that positions a feature of interest within signal data of the signal; parameterizing a portion of the signal data from the signal based upon a hypothesis that a point of interest in the signal data is a position of the feature of interest; determining a posterior probability of the hypothesis being true given the portion of the signal data by combining a prior probability of the hypothesis and a conditional probability of observing the portion of the signal data given the hypothesis.

11 Claims, 3 Drawing Sheets

(51) Int. Cl.
*A61B 5/353* (2021.01)
*A61B 5/355* (2021.01)
*A61B 5/358* (2021.01)
*G06F 17/17* (2006.01)
*G06F 17/18* (2006.01)
*G06F 18/2321* (2023.01)
*G06F 18/2415* (2023.01)
*G16H 50/20* (2018.01)
*G16H 50/70* (2018.01)
*A61B 5/11* (2006.01)

(52) U.S. Cl.
CPC .......... *A61B 5/7221* (2013.01); *A61B 5/7264* (2013.01); *G06F 17/17* (2013.01); *G06F 17/18* (2013.01); *G06F 18/2321* (2023.01); *G06F 18/2415* (2023.01); *G16H 50/20* (2018.01); *G16H 50/70* (2018.01); *A61B 5/1102* (2013.01)

(58) Field of Classification Search
CPC ....... A61B 5/355; A61B 5/358; A61B 5/7221; A61B 5/7264; A61B 5/1102; G16H 50/20; G16H 50/70
See application file for complete search history.

(56) References Cited

U.S. PATENT DOCUMENTS

2007/0239043 A1  10/2007  Patel et al. .................... 600/508
2008/0154487 A1*  6/2008  Krach .................... G01S 19/22
                                                            701/535
2009/0187381 A1*  7/2009  King ................... G06F 18/2433
                                                            702/183
2015/0282755 A1  10/2015  Deriche et al.
2019/0012607 A1*  1/2019  Holliday .................. G06N 7/01

OTHER PUBLICATIONS

Lu et al., "A probability density function method for detecting atrial fibrillation using RâR intervals" Medical Engineering & Physics 31 (2009)) (Year: 2009).*

Swathi et al., "R peak detection and feature extraction for the Diagnosis of heart diseases" 2017 International Conference on Advances in Computing, Communications and Informatics (ICACCI), Udupi, India, 2017 (Year: 2017).*

Vijayavanan et al., "Automatic Classification of ECG Signal for Heart Disease Diagnosis using morphological features" International Journal of Computer Science & Engineering Technology (IJCSET), vol. 5 No. 4 Apr. 2014 (Year: 2014).*

Allen, R. et al., "Time-Domain Signal Analysis", in "Signal Analysis", Dec. 19, 2003, John Wiley & Sons Inc., Hoboken, NJ, pp. 273-382.

Qian, Dong et al., "Drowsiness Detection by Bayesian-Copula Discriminant Classifier Based on EEG Signals During Daytime Short Nap", Apr. 1, 2017, IEEE Transactions on Biomedical Engineering, IEEE Service Center, Piscataway, NJ, vol. 64 No. 4, abstract only.

* cited by examiner

DETERMINING WHETHER A HYPOTHESIS CONCERNING A SIGNAL IS TRUE

CROSS REFERENCE TO RELATED APPLICATION

This patent application is a U.S. National Stage application of International Patent Application Number PCT/EP2018/084111 filed Dec. 10, 2018, which is hereby incorporated by reference in its entirety, and claims priority to EP 17207764.6 filed Dec. 15, 2017.

TECHNOLOGICAL FIELD

Embodiments of the present invention relate to determining whether a hypothesis concerning a signal is true. In particular, some embodiments relate to a method of detection of a recurrent feature of interest within a biological signal, for example, an electrocardiogram (ECG) signal. Some embodiments, may be used for signal encoding to enable more efficient storage and/or transmission of information.

BACKGROUND

It is desirable to detect automatically a recurrent feature of interest within a signal, for example, a biological signal.

Such automation reduces or eliminates the need for a trained human expert to review the signal.

This may be particularly useful in health monitoring applications when it may be desirable to measure features of a biological signal, to assess the health or fitness of a subject.

BRIEF SUMMARY

According to various, but not necessarily all, embodiments of the invention there is provided a method of detection of a recurrent feature of interest within a signal comprising:
obtaining evidence, based on a signal, the evidence including a probability density function for each of a plurality of parameters for parameterizing the signal, including at least one probability density function for a parameter, of the plurality of parameters, that positions a feature of interest within signal data of the signal;
parameterizing a portion of the signal data from the signal based upon a hypothesis that a point of interest in the signal data is a position of the feature of interest;
determining a posterior probability of the hypothesis being true given the portion of the signal data by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data
and
the probability density function for at least one of the plurality of parameters;
using the posterior probability to determine whether or not the hypothesis is true; the method further comprising:
updating at least one of the probability density functions for the plurality of parameters using the parameterization of the portion of the signal data.

If the hypothesis is true, the parameterizing of the signal data based upon the hypothesis may be used for further processes.

In some, but not necessarily all, examples updating at least one of the probability density functions for the plurality of parameters using the parameterization of the portion of the signal data comprises:
using a Bayesian framework to apply a likelihood to a prior probability density function to obtain a posterior probability; and/or
updating at least the probability density function for the parameter that positions the feature of interest within the signal data before determining the posterior probability of the hypothesis being true; and/or
updating the probability density function for the parameter that positions the feature of interest within the signal data by performing a Bayesian update on a prior, the original probability density function for the parameter that positions the feature of interest within the signal, using a likelihood determined by a limited search of the signal data to identify the feature of interest.

In some, but not necessarily all, examples updating at least one of the probability density functions for the plurality of parameters using the parameterization of the portion of the signal data comprises:
updating at least some of the probability density functions for the plurality of parameters after determining the posterior probability of the hypothesis being true.

In some, but not necessarily all, examples the method comprises parameterizing the signal based upon expected parameters that characterize a recurrent feature of interest of a biological signal.

In some, but not necessarily all, examples the method comprises parameterizing the signal based upon expected parameters that characterize a subject's heartbeat.

In some, but not necessarily all, examples the method comprises parameterizing the signal based upon expected parameters of an electrocardiogram signal. In some, but not necessarily all, examples the point of interest is an R-peak of a PQRST complex in the electrocardiogram signal.

In some, but not necessarily all, examples the method comprises: parameterizing the signal based upon an analysis of amplitude variation over time wherein at least some parameters are based on amplitudes of putative waves in the electrocardiogram signal and at least some parameters are based on inter-wave and intra-wave time durations for putative waves in the electrocardiogram signal.

In some, but not necessarily all, determining a posterior probability of the hypothesis being true given the portion of the signal data by combining a prior probability of the hypothesis and a conditional probability of observing the portion of the signal data given the hypothesis, comprises: creating a product by multiplying the conditional probability of observing the portion of signal data given the hypothesis by the prior probability of the hypothesis. In some, but not necessarily all, examples the method comprises normalizing the product by dividing by the sum of a conditional probability of observing the portion of the signal data given the hypothesis multiplied by a prior probability of the hypothesis and a conditional probability of observing the portion of the signal data given a competing hypothesis multiplied by a prior probability of the competing hypothesis.

In some, but not necessarily all, examples the conditional probability of observing the portion of signal data given the hypothesis is based upon a residual/correlation method and/or a deep learning neural network.

According to various, but not necessarily all, embodiments of the invention there is provided an apparatus comprising:
means for obtaining evidence, based on a signal, the evidence including a probability density function for each of a plurality of parameters for parameterizing the signal, including at least one probability density function for a parameter, of the plurality of parameters, that positions a feature of interest within signal data of the signal; means for parameterizing a portion of the signal data from the signal based upon a hypothesis that a point of interest in the signal data is a position of the feature of interest;
means for determining a posterior probability of the hypothesis being true given the portion of the signal data by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data
and
the probability density function for at least one of the plurality of parameters;
means for using the posterior probability to determine whether or not the hypothesis is true;
means for updating at least one of the probability density functions for the plurality of parameters using the parameterization of the portion of the signal data.

The apparatus may comprise means for using the parameterization of the signal data based upon the hypothesis for further processes, if the hypothesis is true.

According to various, but not necessarily all, embodiments of the invention there is provided a computer program that when run on a processor enables the processor to cause:
obtaining evidence, based on a signal, the evidence including a probability density function for each of a plurality of parameters for parameterizing the signal, including at least one probability density function for a parameter, of the plurality of parameters, that positions a feature of interest within signal data of the signal;
parameterizing a portion of the signal data from the signal based upon a hypothesis that a point of interest in the signal data is a position of the feature of interest;
determining a posterior probability of the hypothesis being true given the portion of the signal data by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data
and
the probability density function for at least one of the plurality of parameters;
using the posterior probability to determine whether or not the hypothesis is true;
updating at least one of the probability density functions for the plurality of parameters using the parameterization of the portion of the signal data.

The computer program may enable use of the parameterization of the signal data based upon the hypothesis for further processes, if the hypothesis is true.

According to various, but not necessarily all, embodiments of the invention there is provided a method comprising:
obtaining evidence, based on a signal, the evidence including a probability density function for each of a plurality of parameters for parameterizing the signal, including at least one probability density function for a parameter, of the plurality of parameters, that positions a feature of interest within signal data of the signal;
parameterizing a portion of the signal data from the signal based upon a hypothesis that a point of interest in the signal data is a position of the feature of interest;
determining a posterior probability of the hypothesis being true given the portion of the signal data
by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data
and
the probability density function for at least one of the plurality of parameters;
using the posterior probability to determine whether or not the hypothesis is true;
the method further comprising:
updating at least one of the probability density functions for the plurality of parameters using the parameterization of the portion of the signal data According to various, but not necessarily all, embodiments of the invention there is provided a method of encoding a signal by parameterizing the signal by detection of a recurrent feature of interest within a signal, the method comprising:
obtaining evidence, based on a signal, the evidence including a probability density function for each of a plurality of parameters for parameterizing the signal, including at least one probability density function for a parameter, of the plurality of parameters, that positions a feature of interest within signal data of the signal;
parameterizing a portion of the signal data from the signal based upon a hypothesis that a point of interest in the signal data is a position of the feature of interest;
determining a posterior probability of the hypothesis being true given the portion of the signal data
by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data
and
the probability density function for at least one of the plurality of parameters;

using the posterior probability to determine whether or not the hypothesis is true;
the method further comprising:
updating at least one of the probability density functions for the plurality of parameters using the parameterization of the portion of the signal data.

Then the method may comprise storing the parameters in a memory and/or transmitting the parameters.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

A Primer in Bayes Theorem

Figure 1:
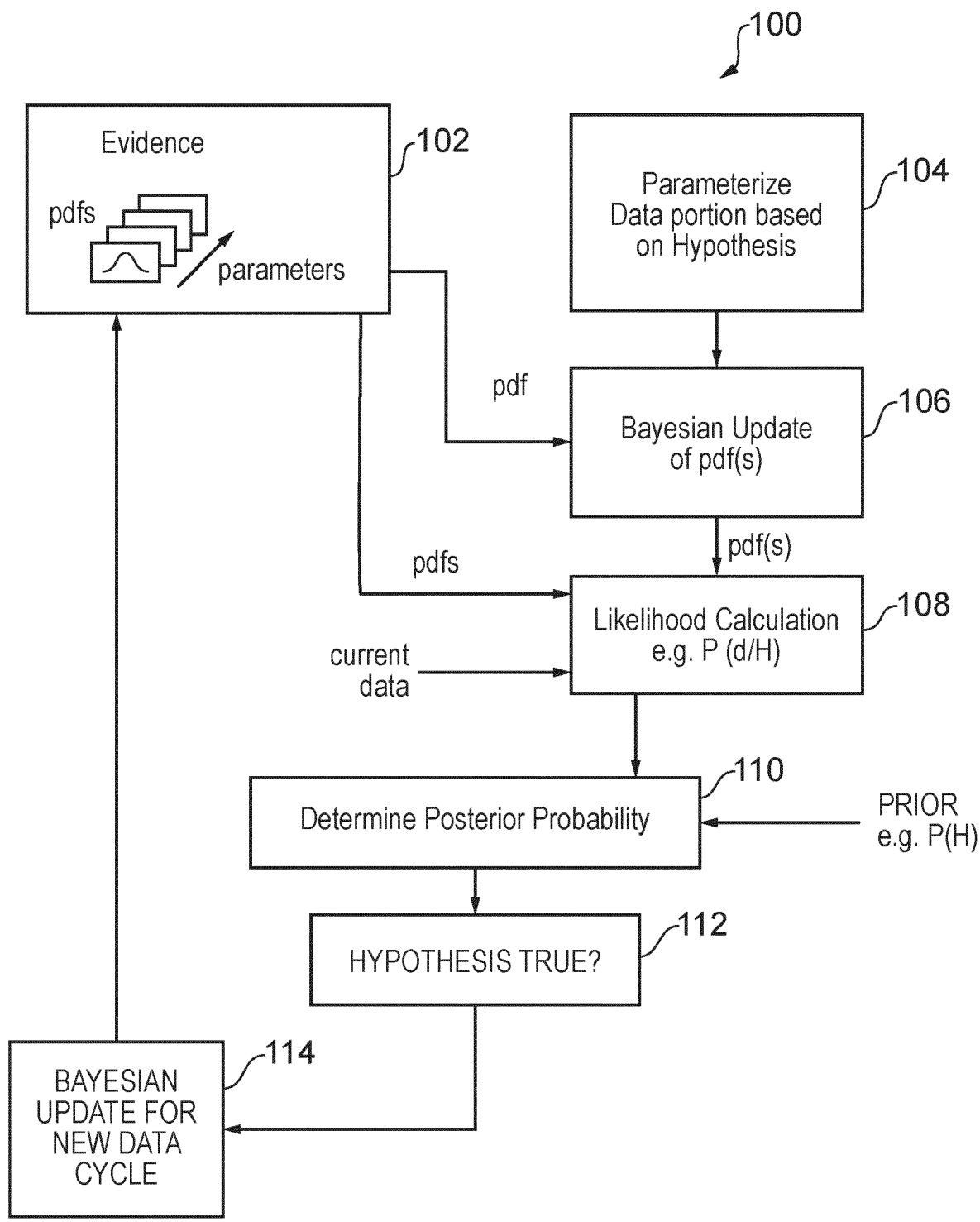
FIG. 1 illustrates an example of a method for detection of a recurrent feature of interest within a signal.

Bayes theorem describes the probability of an event based on ("given") prior knowledge of evidence that might be related to the event.

$$P(A|B)=[P(B|A)*P(A)]/P(B)$$

where A and B are events and $P(B) \neq 0$.

P(A), the 'prior' probability of event A, is the independent probability of event A occurring.

P(B), the 'prior' probability of event B, is the independent probability of event B occurring.

P(A|B) is the conditional probability of event A occurring given that event B occurs.

P(B|A) is the conditional probability of event B occurring given that event A occurs.

In a Bayesian interpretation, probability means a degree of belief and Bayes Theorem links the degree of belief in a proposition before and after accounting for evidence.

In a Bayesian Inference interpretation, a Bayesian Framework, P(A/B) is a posterior probability as a consequence of two antecedents—a prior probability and a likelihood function derived from the observed data (evidence):

A is a hypothesis H whose probability may be affected by evidence.

B is new data d ("current data").
Therefore $$P(H|d)=[P(d|H)*P(H)]/P(d)$$

P(H) is the prior probability. It is an estimate of the probability of H before the new data d.

P(H|d) is the posterior probability. It is the probability of H "given" d, i.e. the probability of H being true given d is observed.

P(d|H) is the likelihood. This is the probability of observing d "given" H is true. It indicates a compatibility of the data with the given hypothesis.

P(d) is a constant for all possible hypotheses.

Thus the posterior probability of a hypothesis is proportional to its prior probability and the likelihood (it's compatibility with the new observed evidence).

In Bayesian updating, the posterior probability becomes the prior probability in a subsequent iteration.

In a Bayesian network, the data d may arise from different sources $s_i$.

$$P(H|d)=P(H|s_1 \& s_2 \ldots s_n)=P(s_1 \& s_2 \ldots s_n|H).$$
$$P(H)/P(s_1 \& s_2 \ldots s_n)$$

This can be presented as a network (e.g. a directed acyclic graph).

For example, if it is assumed $s_i$ are independent given H then $$P(s_1 \& s_2 \ldots s_n|H)=P(s_1.|H). P(s_2.|H) \ldots P(s_n.|H)$$

This can be represented as a simple graph (network) where a node associated with $P(s_1 \& s_2 \ldots s_n.|H)$ is interconnected to separate nodes each representing one of $P(s_1|H). P(s_2.|H) \ldots P(s_n.|H)$ that are not otherwise interconnected.

The general form $P(H|s_1. \& s_2 \ldots s_n)$ can be represented by a more complex directed acyclic graph (network).

If the posterior probability distribution is in the same family as the prior probability distribution, they are conjugate distributions, and the prior is a "conjugate prior" for the likelihood function. For example, the Gaussian family is conjugate to itself (or self-conjugate). If the likelihood function is Gaussian, using a Gaussian prior will a produce a posterior distribution that is also Gaussian.

A probability density function (PDF) is a function of a variable. A sample value of the PDF at any of the possible values of the variable provides a relative likelihood that a value of the variable would equal that sample value. Equivalent expressions of likelihood may be used.

The Method

FIG. 1 illustrates an example of a method 100.

In some but not all examples, the method 100 is a method for detection of a recurrent feature of interest within a signal such as a biological signal. The method may, in some examples, improve the health monitoring of a subject.

The method 100 comprises, at block 102, obtaining evidence, based on a signal, the evidence including a probability density function for each of a plurality of parameters for parameterizing the signal, including at least one probability density function for a parameter, of the plurality of parameters, that positions the feature of interest within the signal data.

The method 100 comprises, at block 104, parameterizing a portion of the signal data based upon a hypothesis that a point of interest in the signal data is a position of the feature of interest.

The method 100 comprises, at block 106, performing an initial update of the probability density of the portion of the signal data describing the occurrence of a certain event. The updated probability density of the portion of the signal data of a given relevant event is based on a Bayesian framework for any form of probability density i.e. gamma, normal destruction etc. The exact form depends on the probability distribution used. The use of conjugate priors simplifies the form.

The block 106 updates at least the probability density function for the parameter that positions the feature of interest within the signal data by performing a Bayesian update on a prior, the original probability density function for the parameter that positions the feature of interest within the signal, using a likelihood determined by a limited search of the parameterized signal data to identify the feature of interest.

Therefore the (updated) conditional probability of observing the portion of the signal data is based at least upon: a parameterization of a portion of the signal data (used to create likelihood) and a probability density function for at least one of the plurality of parameters (the prior).

The method 100, at blocks 108, 110 operates the main Bayesian Framework.

The method 100 comprises, at block 108, estimating the probability of certain observed events from the current data, by making use of the updated probability density function from block 106.

In some examples, the probabilities of certain observed events are combined, as factorized components, to make a main likelihood for use in the Main Bayesian Framework.

$$P(d|H)=P(e1,e2,\ldots|H)=P(e1|H) \times P(e2|H) \times P(e3|H)$$
(assuming events $e1$, $e2$ etc. to be independent)

Each mini-component i.e. $P(e1|H)$ is calculated using one of the updated PDFs corresponding to event $e1$, $e2$ and $e3$ etc.

If the events are not independent but dependent, the factorization of $P(e1, e2, \ldots |H)$ is modified and joint probability densities can be used accordingly. This changes the form of the Bayesian network.

The method 100 then comprises, at block 110, for each point of interest, determining a posterior probability of the hypothesis being true $P(H|d)$ given the portion of the signal data by combining a prior probability of the hypothesis $P(H)$ and the likelihood $P(d|H)$ that is calculated by making use of the updated probability density function and an event observed from the current data.

$$P(H|d)=[P(d|H)*P(H)]/P(d),\text{ for all parameters}$$

The method 100 then comprises, at block 112, using the posterior probability $P(H|d)$ to determine whether or not the hypothesis is true, for each point of interest.

If the hypothesis is true, the parameterizing of the signal data based upon the hypothesis may be used for further processes (not illustrated).

In this example, the initial update at block 106 is conducted using a small part of the current data. The small part is smaller than the original current data size and is used to update the state of belief with limited information. Then at block 108, 110 the method 100 uses the updated PDF (from block 106) and a larger part of the same current data to calculate the probability of the hypothesis given the data $P(H|d)$.

The method 100 then comprises, at block 114, updating at least some of the probability density functions for the plurality of parameters after determining the posterior probability of the hypothesis being true in the light of a new data portion.

Once a new data portion is received, the method 100 repeats.

$P(H)$ is as defined from the beginning and not changed until combined with $P(d|H)$. However, any external event described by a different set of data different from the one utilized to estimate $P(d|H)$ can modify it from iteration to iteration.

Thus the method 100 is a method of detection of a recurrent feature of interest within a signal comprising:

(i) at block 102, obtaining evidence from a signal including a probability density function for each of a plurality of parameters for parameterizing the signal, including at least one probability density function for a parameter, of the plurality of parameters, that positions the feature of interest within the signal data;

(ii) at block 104, parameterizing a portion of signal data from a signal based upon a hypothesis that a point of interest in the signal data is a position of the feature of interest;

(iii) at block 110, determining a posterior probability of the hypothesis being true given the portion of the signal data by combining
 a) a prior probability of the hypothesis and
 b) a conditional probability of observing the portion of the signal data given the hypothesis
 wherein the conditional probability of observing the portion of the signal data given the hypothesis is based at least upon:
  a parameterization of a portion of the signal data and
  a probability density function for at least one of the plurality of parameters;

(iv) at block 112, using the posterior probability to determine whether or not the hypothesis is true, the method 100 further comprising:

at block 106 and/or at block 114, updating at least one of the probability density functions for the plurality of parameters using a parameterization of a portion of the signal data.

If the hypothesis is true, the parameterization of the signal data based upon the hypothesis may be used for further processes (not illustrated).

Although the method 100 has been described with reference to probability density functions, it should be appreciated that instead of probability density functions any suitable measure of an expected relative likelihood of an occurrence of each value of a set of values for the particular parameter for parameterizing the signal may be used. Equivalents of PDFs should be interpreted accordingly.

Updating at least one of the probability density functions for the plurality of parameters using a parameterization of a portion of the signal data comprises: at block 110, using a Bayesian framework to apply a likelihood (from block 108) to a prior probability density function to obtain a posterior probability.

In FIG. 1, updating at least one of the probability density functions for the plurality of parameters using a parameterization of a portion of the signal data comprises: at block 106 updating at least the probability density function for the parameter that positions the feature of interest within the signal data before determining the posterior probability of the hypothesis being true. Updating the probability density function for the parameter that positions the feature of interest within the signal data by performing a Bayesian update on a prior (the original probability density function for the parameter that positions the feature of interest within the signal) using a likelihood determined by a limited search of the signal data to identify the feature of interest.

In FIG. 1, updating at least one of the probability density functions for the plurality of parameters using a parameterization of a portion of the signal data comprises: at block 114 updating at least some of the probability density functions for the plurality of parameters after determining the posterior probability of the hypothesis being true.

Main Bayesian Framework

At block 110, determining a posterior probability of the hypothesis being true given the portion of the signal data by combining a prior probability of the hypothesis and a conditional probability of observing the portion of the signal data given the hypothesis, comprises:
creating a product by multiplying the conditional probability of observing the portion of signal data given the hypothesis by the prior probability of the hypothesis. The product is normalized by dividing by the sum of: a conditional probability of observing the portion of the signal data given the hypothesis multiplied by a prior probability of the hypothesis and a conditional probability of observing the portion of the signal data given a competing hypothesis multiplied by a prior probability of the competing hypothesis.

The conditional probability of observing the portion of signal data given the hypothesis may be based upon a residual/correlation method and/or a deep learning neural network method.

The conditional probability of observing the portion of signal data given the hypothesis may be based upon combining probabilities based on different detection methods, different parameters and/or different corruption scenarios. The corruption scenarios may refer to different combinations of detectable/non-detectable features In the context of ECG, there may be considered to be three important features e.g. R-Peak, T-wave, and P-wave, and different corruption scenarios may refer to all the different combinations of detectable/non-detectable features. For example, the R-Peak is detectable while the other two are noisy, or the other two are clean and R-peak is noisy etc.

In some but not necessarily all examples, the block 104 of the method 100, comprises parameterizing of the signal based upon expected parameters that characterize a recurrent feature of interest of a biological signal. A distinction is made between the actual values (unknown) and expected or reference values. What actually characterizes an actual signal is different to what is expected to characterize an expected signal. Parameterization is based on expectation.

Figure 2B:
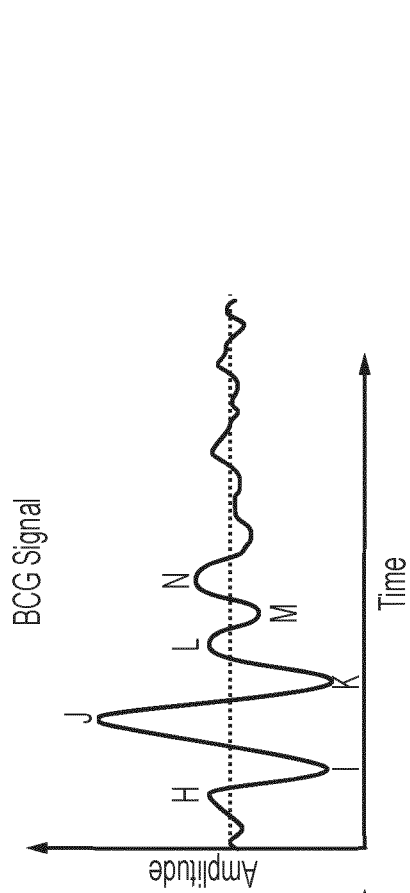
FIGS. 2A, 2B, 2C, 2D illustrates examples of biological-signals.
Figure 2A:
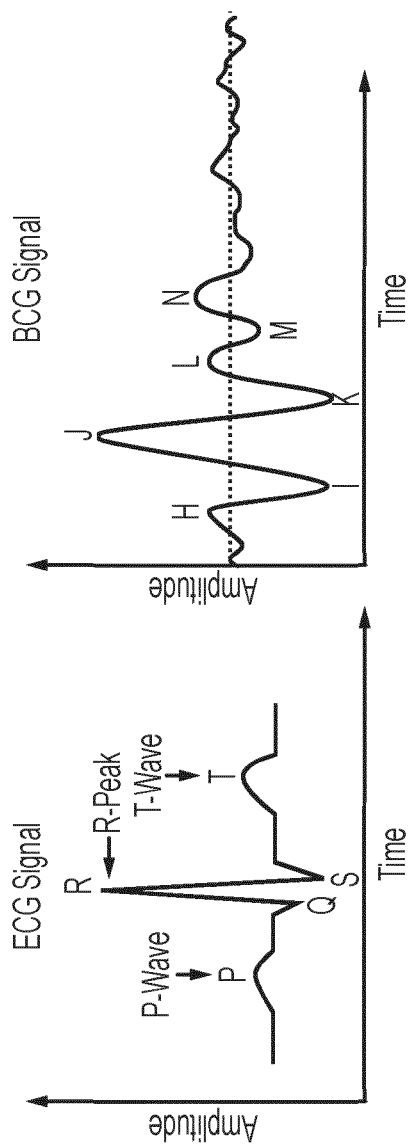
Figure 2D:
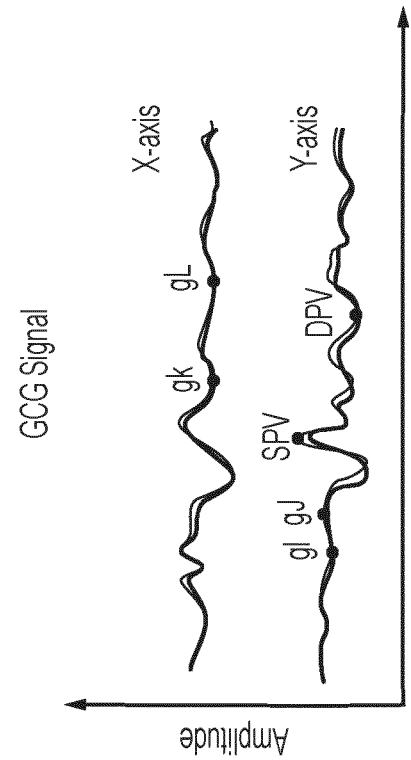
Figure 2C:
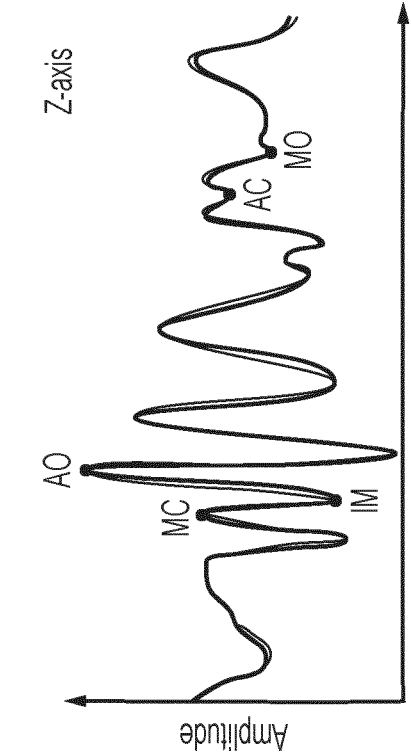

FIGS. 2A, 2B, 2C illustrates examples of a biological signal. A morphology of interest can be any recurrent morphology in a biological signal. FIG. 2A illustrates an example of an electrocardiogram (ECG) signal. FIG. 2B illustrates an example of a ballistocardiogram (BCG) signal. FIG. 2C illustrates an example of a seismocardiogram (SCG). FIG. 2D illustrates an example of a gyrocardiogram (GCG) signal. Gyrocardiography (GCG) is a non-invasive technique for assessing heart motions by utilizing a gyroscope that is attached to the chest of an individual as a sensor of angular motion.

Figure 3:
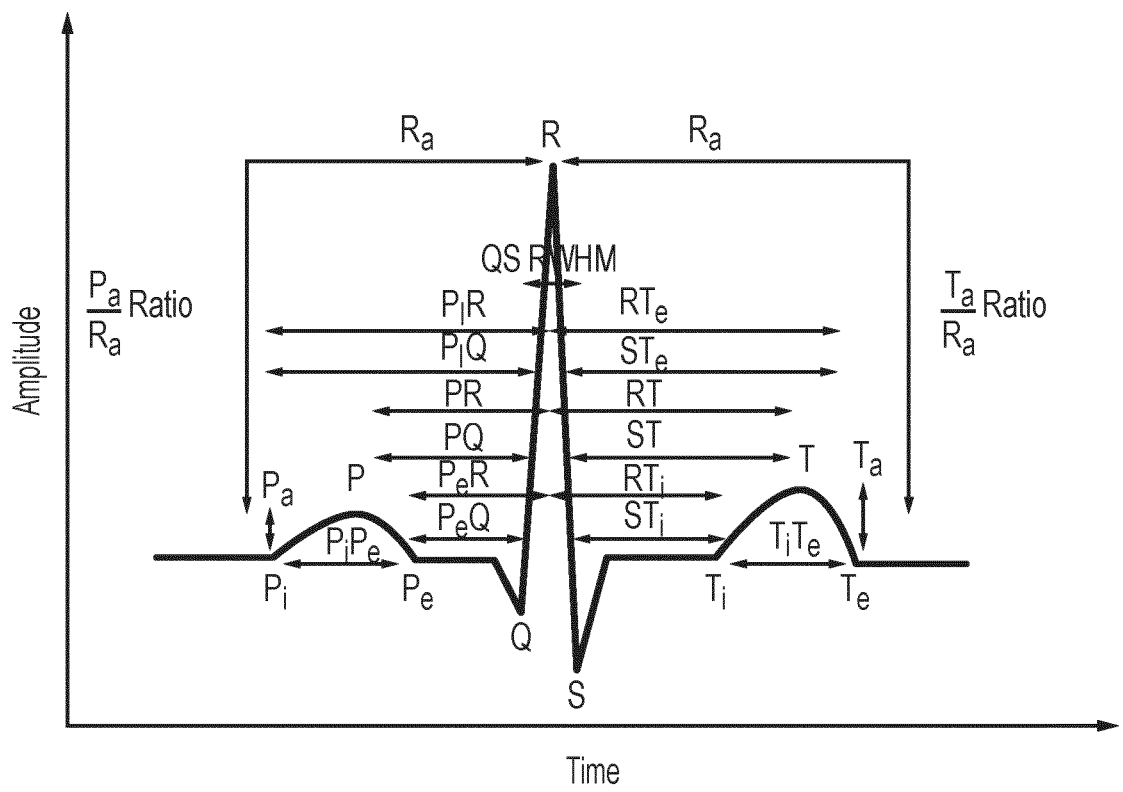
FIG. 3 illustrates an example of parameters for an electrocardiogram.

FIG. 3 illustrates an example of an electrocardiogram. The morphology of interest can be QRS-Complex and thus P-wave and T-wave are utilized as evidence. The morphology of interest can be T-wave and thus P-wave and QRS-complex are utilized as evidence. The morphology of interest can be P-wave and thus T-wave and QRS-complex are utilized as evidence.

The method 100 will now be described, for this example. However, the method may also be used for other signals:

The expected parameters may characterize a subject's heartbeat. The signal may be parameterized based upon expected parameters of an electrocardiogram signal.

Thus at block 104, the method 100 comprises parameterizing a portion of signal data based upon a hypothesis that a point of interest in the signal data is a position of the feature of interest. For example, the feature of interest is an R-peak of a PQRST complex in the electrocardiogram signal.

At block 104, the method may comprise: parameterizing the signal based upon an analysis of amplitude variation over time wherein at least some parameters are based on amplitudes of putative waves (reference waves) in the electrocardiogram signal and at least some parameters are based on inter-wave and intra-wave time durations for putative waves in the electrocardiogram signal. In this example, the waves include the P-wave, the QRS complex and the T-wave.

The parameterization of the signal at block 104 is based upon parameters for an ECG signal. The parameters may be, as illustrated in FIG. 3:

Q=Starting point of QRS-Complex
R=Maximum point of QRS-Complex
S=End point QRS-Complex
$T_i$=Starting point of T-Wave
T=Maximum point of T-Wave
$T_e$=End point of T-Wave
$P_i$=Starting point of P-Wave
P=Maximum point of P-Wave
$R_a$=R peak amplitude
$P_a$=P wave amplitude
$T_a$=T wave amplitude
$P_e$=End point of P-Wave
$T_iT_e$=Distance between $T_i$ and $T_e$
$P_iP_e$=Distance between $P_i$ and $P_e$ $$\frac{T_a}{R_a} = \text{Ratio between } T \text{ amplitude and } R \text{ amplitude}$$

$$\frac{P_a}{R_a} = \text{Ratio between } P \text{ amplitude and } R \text{ amplitude}$$

PQ=Distance between P and Q
ST=Distance between S and T
$P_i\,T_e$=Distance between $P_i$ and $T_e$
RR=Distance between two consecutive R-Peaks
Evidence, as generated at block 102, may be determined based on the parameters
Evidence One ($E_1$)=QRS Morphology
Evidence Two ($E_2$)=$T_iTT_e$ Morphology
Evidence Three ($E_3$)=PiPPe Morphology
Evidence Four ($E_4$)=$P_iT_e$ Morphology
Evidence Five ($E_5$)=QTe Morphology
Evidence Six ($E_5$)=$P_iS$ Morphology
Evidence Seven ($E_7$)=$R_a$
Evidence Eight ($E_8$)=$P_a$
Evidence Nine ($E_9$)=$T_a$ $$\text{Evidence Ten}(E_{10}) = \frac{T_a}{R_a}\text{Ratio}$$

$$\text{Evidence Eleven}(E_{11}) = \frac{P_a}{R_a}\text{Ratio}$$

Evidence Twelve ($E_{12}$)=QS FWHM
Evidence Thirteen ($E_{13}$)=$P_iR$
Evidence Fourteen ($E_{14}$)=TiQ
Evidence Fifteen ($E_{15}$)=PR
Evidence Sixteen ($E_{16}$)=PQ
Evidence Seventeen ($E_{17}$)=PeR
Evidence Eighteen ($E_{18}$)=PeQ
Evidence Nineteen ($E_{19}$)=RTe
Evidence Twenty ($E_{20}$)=STe
Evidence Twenty One ($E_{21}$)=RT
Evidence Twenty Two ($E_{22}$)=ST
Evidence Twenty Three ($E_{23}$)=RT,
Evidence Twenty Four ($E_{24}$)=ST, Evidence Twenty Five ($E_{25}$)=TiTe
Evidence Twenty Six ($E_{26}$)=PiPe
Evidence Twenty Seven ($E_{27}$)=RR
Evidence Twenty Eight ($E_{28}$)=$P_iT_e$ All evidence, including $E_1$ up to $E_{28}$ can be utilized. Alternatively or additionally, any combinations of evidence can be utilized. E.g. $E_1$-$E_5$, $E_2$-$E_{20}$, $E_{20}$-$E_{28}$ etc.

Alternatively or additionally, any number of newly generated features that utilize any combinations of evidence can be utilized. E.g. $E_1$ combined with $E_2$-$E_1$, $E_2$, $E_1$ $E_2$ and $E_3$ combined—$E_1E_2E_3$ etc.

Supervised Approach for Evidence Generation at Block 102

The user defines one or more regions within the dataset of the signal data to extract all necessary evidence ($E_1$ up to $E_{28}$).

In this example, the user may be a medical/non-medical expert/non-expert, a wearable device user, or a robot system selecting a region of the recorded data on a personal computer, tablet, phone, wearable device or any electronic device with a touch screen or no-touch screen, that has the capability to display any biological signal.

In one form of the embodiment, the region selection process can be performed in real time, i.e. when a biological signal is being recorded and in another form the selection can be performed after the recording has been completed.

For the selected region, all positive (upward) and negative (downward) peaks are detected. The peak detection of selected region could include but is not limited to regression based, correlation based, neural network based, or any similarity measure, or hierarchical process used to distinguish all peaks and/or peak like features within the selected region using either a single or multiple peak models.

The first N number of tallest peaks is designated as the R-point of QRS-complex for a positive peak scenario, and the first N number of minimum points is designated as the R-point of QRS-complex for a negative peak scenario. The number N is typically greater than 1 and is predetermined or dynamically varied. N may be set by the algorithm developer as a default value. It could be 4, 5 etc.

Unsupervised Approach for Evidence Generation at Block 102

The system automatically selects all relevant regions from the initial incoming portion of the data to learn the features and generate their corresponding probability density functions.

First, for the incoming data portion, all peaks are detected and the peak maximas or mimimas are identified. Given this information, two consecutive expectation maximization clustering processes are performed.

In the first clustering step, the detected peaks are clustered based on their amplitude. In the simplest case, the number of expected clusters can be set to 3. The 3 clusters are the minimum, maximum, and median of the maximum and minimum amplitudes of the detected peaks. The $1^{st}$ cluster is assumed to capture small noisy peaks, the $2^{nd}$ cluster midpoint peaks such as T-waves and P-waves and possible interference at that amplitude level, and the $3^{rd}$ cluster is assumed to capture peaks with the greatest amplitude magnitude. The system will automatically pick the $3^{rd}$ cluster for the next step. Any appropriate number of clusters can be implemented.

At this stage, several of the initially detected peaks have been filtered and thus only the peaks falling in the $3^{rd}$ cluster are remaining. Further clustering is performed based on the peaks width at half maximum criteria (FWHM). Once the peak widths have been estimated, the presence/absence of 2 clusters are checked. The cluster with the minimum FWHM is selected as a potential R-peak cluster. This is based on an assumption that T-waves and P-waves usually are wider peaks. Any appropriate number of clusters can be implemented.

Thus the final cluster selected will consist of a group of peaks with the highest amplitude and narrowest FWHM and the system labels them as the most probable R-peaks to extract features from. However, before obtaining evidence takes place, further assessment takes place. For example, if the number of peaks remaining in the final cluster is less than a minimum value a new data portion is initiated. However, if the minimum number of peaks criteria is fulfilled (number of peaks remaining in the final cluster is equal to or more than the minimum value), further analysis will take place.

Given the above criterion is fulfilled, a matrix containing QRS-complex morphologies from the hypothetically selected peaks is generated. For example, if 5 peaks were remaining in the final step of the above clustering process, those five peaks are considered the location of R-peaks, and thus all data points within the QRS-complex of each R-peak are extracted and concatenated to generate a QRS-complex morphology matrix.

Given the morphology matrix, either a probabilistic or deterministic similarity determination can be performed to check if all the morphologies are in fact QRS-complex. If this criterion is not fulfilled, the whole process is initialized from the beginning for a new data portion.

Approach for Evidence Generation at Block 102 Common to Supervised and Unsupervised Approach Whether the supervised or unsupervised approach is followed, given the detected R-point locations, all relevant points within the ECG signal (i.e. Q, S, $P_i$, P, $P_e$, $T_i$, T, and $T_e$) can be identified.

Given all the identified points, the selected region can be segmented into N number of compartments, where each compartment will consist of a QRS-complex, T-Wave, and P-Wave. Given this N number of compartments, all necessary features including morphologies and distance measures (i.e. QRS-morphology, QS distance etc.) are designated as an evidence (e.g. $E_1$ to $E_{28}$). Thus there is N number of $E_1$ to $E_{28}$ pieces of evidence designated.

The N number of $E_1$ to $E_{28}$ evidence designated can then be organized in a way where all similar features will fall in to the same group and thus result in a vector or a matrix depending on the size of the feature. For example, $E_{12}$ (QS FWHM) for all N number of compartments can be grouped together to create a vector where each row represents the feature from each compartment:

$$QS\ FWHM\ Vector = \begin{bmatrix} QS\ FWHM - 1 \\ QS\ FWHM - 2 \\ QS\ FWHM - 3 \\ QS\ FWHM - 4 \\ \cdot \\ \cdot \\ QS\ FWHM - N \end{bmatrix}$$

In a similar fashion, if the information for $E_1$ (QRS Morphology) from all compartments are grouped together, it will generate a m×n matrix (row×column) where each column is the feature from a given compartment and each row represents a data point from that compartment.

$$QRS \text{ Morphology Matrix} = \begin{bmatrix} QRS \text{ Morphology-}11 & \ldots & QRS \text{ Morphology-}1n \\ QRS \text{ Morphology-}21 & \ldots & QRS \text{ Morphology-}2n \\ QRS \text{ Morphology-}31 & & QRS \text{ Morphology-}3n \\ \cdot & \ldots & \cdot \\ QRS \text{ Morphology-}m1 & & QRS \text{ Morphology-}mn \end{bmatrix}$$

Given the vectors, a probability density function (PDF) that describes the probability distribution of each feature as a variable is generated using each vector. For example, in the simplest case scenario, the vector representing $E_{12}$ (QS FWHM) can be considered to follow a normal probability distribution, thus the parameters of the normal probability density can be approximated as the mean and standard deviation of the vector itself. However, the embodiment is not limited to normal distribution but any probability density that is appropriate to represent the distribution of the features can be implemented.

The probability density function representing the distribution of features in a matrix can be generated either by utilizing a vector representation of the matrix or the original matrix itself. For example, to obtain a simplified vector representation of the matrix, a residual based or correlation based approach may be used. In general, any similarity measure based approach can be applied. In one approach, a reference vector can first be generated through a column-wise-averaging of the matrix (across compartments). This reference vector can then be used to obtain residuals between the reference vector and each column of the original features matrix. The residual of each column is then squared and summed. This process will result in residuals sum of squared (RSS) vector where each entry carries information from each feature in each column of the original matrix, and thus the entire matrix represented as a vector.

In a similar fashion, instead of calculating the residuals, the reference vector described above can also be used to generate a correlation distribution by calculating the correlation (COR) between the reference vector and each column of the matrix, once again collapsing the matrix into a vector where each entry in the vector carries information from each column feature of the original matrix. The generated vector can then be used to estimate a probability density function.

The features along with their probability density are stored in a memory.

Given $E_{28}$ (RR) and its probability distribution, the most probable hypothetical locations for N number of future R-Peak locations along with their uncertainties are generated. This estimate takes into account the possible error propagation that might be present in the estimate, that increases the uncertainty over time.

Bayesian Framework

Let us consider two competing hypotheses:
$H_1$=Point of Interest is the location of R-peak
$H_2$=Point of interest is not the location of R-peak
A Bayesian Framework can be defined:

$$P(H_1 \mid D, I) = \frac{P(D \mid H_1, I)P(H_1 \mid I)}{[P(D \mid H_1, I)P(H_1 \mid I)] + [P(D \mid H_2, I)P(H_2 \mid I)]}$$

$P(D|H_1, I)$=The probability of the data D given the hypothesis and all relevant existing evidence (likelihood)

$P(H_1|I)$=The prior probability of the hypothesis (Prior)
D=The data is parametrized into several pieces of evidence referring to the relevant and distinct features in the signal i.e. $E_1, E_2, \ldots E_n$ Initial update of probability density function(s) at block 106

The initial step in R-peak detection for the new data portions is to first update the probability density generated using the previous data portion that describes the most likely location of future R-peaks (PDF for $E_{27}$). This corresponds to block 106.

Given the probability distribution of where the true R-peak location might be, given the learned R-R interval information from the previous portion of the data, a vertical and horizontal motion will take place within a certain window of limited size to locate the most likely position where R-peak could be located at. This is a limited search. This process is a low level expectation maximization step that expects a certain amplitude and morphology within the vicinity of the initial guess to update the probability density of a single evidence ($E_{27}$) using Bayesian framework. This updated density will later on be utilized, at block 108, for estimating the likelihood used in calculating the main probability of interest $P(H_1|D,I)$ at block 110.

Block 106 is applied for all hypothetical R-peak locations probability distributions. Thus given the updated probability densities, all regions that fall outside a certain limit of that distribution (e.g. ±3σ) are assigned a flat probability density. This process takes into account the possibility for any random region to consist of an unexpected arrhythmic beat.

Given the detected QRS-complex consisting regions (e.g. $P(H_1|D,I)>0.5$), some of the information acquired from the evidence gathering phase 102 (i.e. probability density, morphology etc.) is updated using Bayesian framework. The embodiment can include updating of any given number of the probability densities while keeping some fixed if necessary.

At block 110, the posterior probability $P(H_1|D,I)$ is computed for all data points within the data set in a moving window. At any given time, the data point being observed is referred to as the point of interest, and thus the window is defined by placing the point of interest at the center. The size of the window on the other hand is defined based on the information learned during the evidence generation phase and its probability density i.e. Evidence Twenty Eight $(E_{28})=P_iT_e$ Likelihood Determination at Block 108

In one embodiment two main methods are used to extract information from data to obtain $P(D|H_1, I)$, the likelihood. The first method utilizes residuals/correlation approach, and the second method utilizes a deep learning neural network. The notion of simultaneously utilization several methods can be expressed in the likelihood by introducing a new parameter M (method) and marginalizing it as follows:

$$P(D,M|H_1,I)=[P(D|M_1,H_1,I)P(M_1|H_1,I)]+[M_1|M_2,H_1,I)P(M_2|H_1,I)]$$

$P(D|M_1, H_1, I)$ refers to the probability of data under the supposition hypothesis $H_1$ is true and method one ($M_1$, residual/correlation) is used and any relevant background information (I)), while $P(D|M_2, H_1, I)$ refers to the probability of data under the supposition hypothesis $H_1$ is true and method two ($M_2$, deep learning) is used and any relevant background information (I). $P(M_1|H_1, I)$ and $P(M_2|H_i, I)$ refers to the probability of each method before the data is observed. In an uninformed state without any preference for each method, a flat probability can be assigned. If however there is any reasonable preference for any given model corresponding information extraction reliability, the probabilities can be adjusted accordingly.

When the data (D) is further expanded as different pieces of evidence and factorized the likelihood will appear as follows:

$$P(D|H_1,I)=P(D,M|H_1,I)=[(P(E_1|M_1,H_1,I)P(E_2|M_1,H_1,I)P(E_3|M_1,H_1,I)\ldots P(E_n|M_1,H_1,I)P(M_1|H_1,I)]+ [P(D|M_2,H_1,I)P(M_2|H_1,I)]$$

Taking into account the deep learning model is trained with a single form of data input, further expansion into several pieces of evidence for $M_2$ is not necessary. In another embodiment, the neural network can also be utilized with different and distinct pieces of evidence from the data as well.

In method one ($M_1$), in one embodiment residual based and correlation based approaches are employed. In another embodiment other additional sub methods or any number of combination of sub methods can be employed. The correlation analysis helps estimate any association between a known morphology and an observed one, while the residual based approach helps to keep track of shape based analysis. Thus two distinct methods can be exploited under the umbrella of method one ($M_1$) by once again introducing another parameter S referring to a sub method into the expressions containing $M_1$ and marginalizing it as follows:

$$P(D|H_1,I) = \left[\left[\sum_{i=1}^{2}\binom{P(E_1|S_i,M_1,H_1,I)P(E_2|S_i,M_1,H_1,I)}{P(E_3|S_i,M_1,H_1,I)\ldots P(E_n|S_i,M_1,H_1,I)}\right)\right.$$
$$\left.P(S_i|M_1,H_1,I)\right]P(M_1|H_1,I)\right] + [P(D|M_2,H_1,I)P(M_2|H_1,I)]$$

In addition to such form of evidence extraction process, all possible case scenarios in regards to the presence/absence of data corruption can also be modelled. This modelling consists of the following possible putative scenarios:

1. Clean QRS-Complex, T-wave, and P-wave region
2. Clean QRS-Complex, and T-wave, while P-wave region is corrupted
3. Clean QRS-Complex, and P-wave region, while T-wave region is corrupted
4. Clean QRS-Complex, while T-Wave and P-Wave regions are corrupted In order to include this scenarios into the likelihood calculation, once again a new parameter C referring to the above listed case scenarios is introduced and marginalized as follows:

$$P(D|H_1,I) = \left[\left[\sum_{i=1}^{4}\left[\sum_{j=1}^{4}\right.\right.\right.$$
$$\left(\begin{array}{c}P(E_1|C_j,S_i,M_1,H_1,I)P(E_2|C_j,S_i,M_1,H_1,I)\\ P(E_3|C_j,S_i,M_1,H_1,I)\ldots P(E_n|C_j,S_i,M_1,H_1,I)\end{array}\right)*$$
$$\left.\left.P(C_j|S_i,M_1,H_1)\right]P(S_i|M_1,H_1,I)\right]P(M_1|H_1,I)\right] +$$
$$[P(D|M_2,H_1,I)P(M_2|H_1,I)]$$

On the assumption $E_1$ refers to a given observed signal morphology, $P(E_1|C_j, S_i, M_1, H_1, I)$ would then be the probability of the observed morphology under the supposition hypothesis $H_1$ is true and method one ($M_1$) is used consisting of for example the first possible case scenario (i=1), residual based method (j=1), and any additional relevant background information.

In the equations described above, an assumption of independence between different pieces of evidence is utilized. However, in other embodiments dependence between pieces of evidence could also be modelled and thus a joint probability density can be generated and utilized.

The above described equations for the case of hypothesis $H_1$ also applies for hypothesis $H_2$. However, the probability density function utilized for both competing cases differ. For example, consider $P(E_1|C_1, S_1, M_1, H_1, I)$ where $E_1$ is evidence relating to QRS-complex morphology. In this expression, $H_1$ is assumed to be true, and sub method $M_1$ uses residuals as a source of evidence. The probability density function obtained by the expression should be able to describe the distribution of RSS (residual sum of square) between the observed morphology and the designated morphology assumed to represent the correct QRS-complex morphology. This RSS attempts to capture the possible systematic as well as biological variations that occur within the signal. The RSS distribution observed in a given region between the reference (average) morphology and other detected QRS-complex morphology can be used in the likelihood calculation when an additional incoming data portion enters the system. In addition, this probability density can also be updated dynamically based on newly detected morphologies, and their corresponding RSS distribution using a Bayesian framework.

Similarly, in order to capture the possible RSS distribution between designated QRS-morphology and noise, a QRS-free region can be utilized. The same approach described above also applied when correlation based method is considered and all necessary probability distributions are derived and continuously updated as more information is gathered.

Posterior Probability at Block 110

The process of calculating the final posterior Probability for Hypothesis, at block 110 requires a prior and a likelihood. The prior probability is the probability at the beginning of the analysis when the hypothesis itself is defined. The likelihood is calculated, at block 108, by utilizing the data (any piece of evidence) and the updated knowledge (PDFs etc.) including those updated at block 106. Using Bayes' theorem, the prior can be updated with the likelihood which can be used to decide whether or not the Hypothesis is true/false at block 112.

Updating the Evidence at Block 114

The Process of updating evidence at block 114 includes but is not limited to: updating the PDF related to a location of the feature of interest in an incoming new data portion; updating PDF related to morphology of the feature of interest; any PDF generated during block 102 (evidence generation) can be updated. For updating any of the PDFs the following process takes place: the original PDF obtained during evidence generation process 102 is used as a prior; for the likelihood, a small portion of the data from within the new data portion is utilized. How this small portion is defined is based on the prior PDF itself. For example if the prior PDF was assumed to follow a normal distribution and had the parameters µ=10, ∂=5, for mean and standard deviation, respectively, one way would be to utilize all data points falling within 10±(2∂), as an example, to generate a new PDF for the likelihood. Then Bayes' theorem is used to update the prior PDF with the new PDF.

Signals

Data may include but is not limited to ECG, PPG, BCG, GCG, SCG, accelerometer, etc. Therefore the posterior probability calculated at block 110 can also be expressed as follows:

$$P(H_1 | \text{Data}, I) = \frac{P(ECG, PPG, BCG, SCG, GCG... | H_1, I)P(H_1 | I)}{[P(ECG, PPG, BCG, SCG, GCG... | H_1, I)P(H_1 | I)] + [P(ECG, PPG, BCG, SCG, GCG... | H_2, I)P(H_2 | I)]}$$

In one embodiment all available biological and non-biological signals are utilized. In another embodiment any combination of signals can be utilized.

In one embodiment all pieces of evidence extracted from each biological or non-biological signal is utilized while in another embodiment any combination of pieces of evidence can be utilized The hypothesis can refer to any relevant information in a biological signal and is not limited to ECG. Each hypothesis has its own prior probability generated without having to look at the data and this prior probability is not modified until its updated at the end of the method 100 at after block 112. Examples of hypothesis include but are not limited to: there is an R-Peak in ECG Signal; there is a I-Valley in BCG Signal; there is a SPV peak in GCG Signal.

Evidence generated at block 102 includes but is not limited to: bio-signal morphology that defines feature of interest; uncertainty of the morphology defined by a PDF; a possible location of feature of interest for future incoming data; uncertainty of location of feature of interest for future incoming data; any relevant evidence and its uncertainty that helps to determine if the Hypothesis is True/False.

Apparatus

Figure 4:
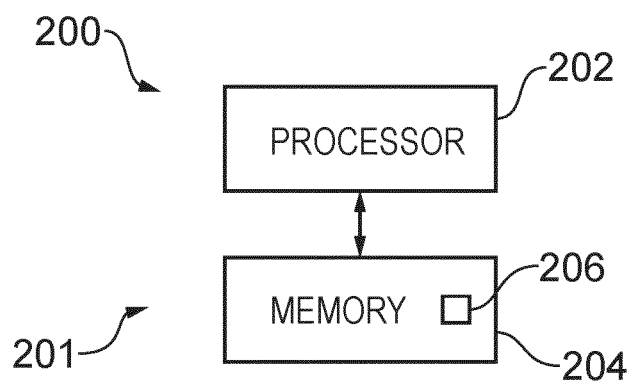
FIG. 4 illustrates an example of an apparatus for performing the method.

FIG. 4 illustrates an example of an apparatus 200 comprising means for performing the method 100 as described above. The apparatus 200 may, for example, comprise a controller 201.

The apparatus 200 is, in some but not necessarily all examples, a health monitoring apparatus that measure features of a biological signal, to assess the health or fitness of a subject. The health monitoring apparatus 200 may as a consequence of the performance of the method 100 detect anomalies in a biological signal. The biological signal may be received from one or more sensors comprised in the apparatus 200

Implementation of a controller 201 may be as controller circuitry. The controller 201 may be implemented in hardware alone, have certain aspects in software including firmware alone or can be a combination of hardware and software (including firmware).

As illustrated in FIG. 4 the controller 201 may be implemented using instructions that enable hardware functionality, for example, by using executable instructions of a computer program 206 in a general-purpose or special-purpose processor 202 that may be stored on a computer readable storage medium (disk, memory etc) to be executed by such a processor 202.

The processor 202 is configured to read from and write to the memory 204. The processor 202 may also comprise an output interface via which data and/or commands are output by the processor 202 and an input interface via which data and/or commands are input to the processor 202.

The memory 204 stores a computer program 206 comprising computer program instructions (computer program code) that controls the operation of the apparatus 200 when loaded into the processor 202. The computer program instructions, of the computer program 206, provide the logic and routines that enables the apparatus to perform the methods illustrated in FIG. 1. The processor 202 by reading the memory 204 is able to load and execute the computer program 206.

The apparatus 200 therefore comprises:

at least one processor 202; and at least one memory 204 including computer program code the at least one memory 204 and the computer program code configured to, with the at least one processor 202, cause the apparatus 200 at least to perform:

obtaining evidence from a signal including a probability density function for each of a plurality of parameters for parameterizing the signal, including at least one probability density function for a parameter, of the plurality of parameters, that positions the feature of interest within the signal data;

parameterizing a portion of signal data from a signal based upon a hypothesis that a point of interest in the signal data is a position of the feature of interest;

determining a posterior probability of the hypothesis being true given the portion of the signal data by combining a prior probability of the hypothesis and a conditional probability of observing the portion of the signal data given the hypothesis, wherein the conditional probability of observing the portion of the signal data given the hypothesis is based at least upon:

a parameterization of a portion of the signal data and a probability density function for at least one of the plurality of parameters;

using the posterior probability to determine whether or not the hypothesis is true;

the method further comprising:

updating at least one of the probability density functions for the plurality of parameters using a parameterization of a portion of the signal data.

The computer program 206 may arrive at the apparatus 200 via any suitable delivery mechanism. The delivery mechanism may be, for example, a non-transitory computer-readable storage medium, a computer program product, a memory device, a record medium such as a Compact Disc Read-Only Memory (CD-ROM) or Digital Versatile Disc (DVD), an article of manufacture that tangibly embodies the computer program 206. The delivery mechanism may be a signal configured to reliably transfer the computer program 206. The apparatus 200 may propagate or transmit the computer program 206 as a computer data signal.

Although the memory 204 is illustrated as a single component/circuitry it may be implemented as one or more separate components/circuitry some or all of which may be integrated/removable and/or may provide permanent/semi-permanent/dynamic/cached storage.

Although the processor 202 is illustrated as a single component/circuitry it may be implemented as one or more separate components/circuitry some or all of which may be integrated/removable. The processor 202 may be a single core or multi-core processor.

Application

As previously mentioned, FIGS. 2A, 2B, 2C illustrates examples of a biological signal. A morphology of interest can be any recurrent morphology in a biological signal. FIG. 2A illustrates an example of an electrocardiogram (ECG) signal. FIG. 2B illustrates an example of a ballistocardiogram (BCG) signal. FIG. 2C illustrates an example of a seismocardiogram (SCG). FIG. 2D illustrates an example of a gyrocardiogram (GCG) signal. Gyrocardiography (GCG) is a non-invasive technique for assessing heart motions by utilizing a gyroscope that is attached to the chest of an individual as a sensor of angular motion.

The methods and apparatus described above detect automatically one or more recurrent features of interest within a signal, for example, a biological signal.

Such automation reduces or eliminates the need for a trained human expert to review the signal and converts the signal as measured to an intelligently parameterized signal is a form that is machine readable and machine processable. The signal is intelligently parameterized based on the recurrent features of interest that define that signals morphology.

The signal, parameterized based on its recurrent features of interest, may be used as an input to further processes.

These processes may occur locally or remotely. They may, for example, be cloud based.

These processes may use machine learning algorithms to identify anomalies in the bio-signal and/or create training data for the machine learning algorithms. Examples of machine learning algorithms include, for example, neural networks, hidden Markov models, logistic regression etc.

Alternatively or additionally, the processes may enable health monitoring applications when it may be desirable to measure features of a biological signal, to assess the health or fitness of a subject.

Alternatively or additionally, the processes may enable a warning to be generated that alerts a subject or someone else. The warning may, for example, warn the subject or someone else that an anomaly has been detected or that a threshold has been exceeded. The warning may be an audible warning. The warning may be a message communicated through a communication system.

The apparatus may, for example, be a personal, wearable apparatus.

The apparatus may, for example, be a health monitor apparatus or a vital-signs monitor apparatus.

The parameterization of the signal reduces the amount of bandwidth required to store or communicate a signal. The Nyquist-Shannon theorem states that a signal must be sampled at at least twice the highest frequency of interest within the signal. This can produce very large amounts of data which needs to be stored and/or transmitted. The reduction of a time-varying biological signal into higher-level parameters that characterize the recurrent features of interest for that signal's morphology, significantly reduces the bandwidth required.

The above methods and apparatus therefore relate to a method of parameterizing a signal by detection of a recurrent feature of interest within a signal or a method of reducing bandwidth/entropy of a signal by detection of a recurrent feature of interest within a signal or a method of encoding for efficient storage or transmission of a signal by detection of a recurrent feature of interest within a signal.

The methods comprise:
obtaining evidence, based on a signal, the evidence including a probability density function for each of a plurality of parameters for parameterizing the signal, including at least one probability density function for a parameter, of the plurality of parameters, that positions a feature of interest within signal data of the signal;
parameterizing a portion of the signal data from the signal based upon a hypothesis that a point of interest in the signal data is a position of the feature of interest;
determining a posterior probability of the hypothesis being true given the portion of the signal data
by combining
a prior probability of the hypothesis
and
a conditional probability of observing the portion of the signal data given the hypothesis,
wherein the conditional probability of observing the portion of the signal data given the hypothesis is based at least upon:
the parameterization of the portion of the signal data and
the probability density function for at least one of the plurality of parameters;
using the posterior probability to determine whether or not the hypothesis is true;
the method further comprising:
updating at least one of the probability density functions for the plurality of parameters using the parameterization of the portion of the signal data.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as Field-Programmable Gate Arrays (FPGA), Application Specific Integrated Circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in FIG. 1 may represent steps in a method and/or sections of code in the computer program 206. The illustration of a particular order to the blocks does not necessarily imply that there is a required or preferred order for the blocks and the order and arrangement of the block may be varied. Furthermore, it may be possible for some blocks to be omitted.

As used here 'module' refers to a unit or apparatus that excludes certain parts/components that would be added by an end manufacturer or a user. the apparatus 10 may be a module.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of detection of a recurrent feature of interest within an electrocardiogram signal comprising:
obtaining evidence, based on the electrocardiogram signal from one or more sensors for the electrocardiogram signal for a subject's heart, the evidence including a probability density function for each of a plurality of parameters for parameterizing the electrocardiogram signal, including at least one probability density function for a parameter, of the plurality of parameters, that positions the recurrent feature of interest within signal data of the electrocardiogram signal, wherein the feature of interest is an R-peak of a PQRST complex in the electrocardiogram signal;
parameterizing a portion of the signal data from the electrocardiogram signal based upon a hypothesis that a point of interest in the signal data is a position of the recurrent feature of interest, wherein the parameterizing comprises parameterizing the portion of the signal data based upon expected parameters that characterize the recurrent feature of interest of the electrocardiogram signal;
determining a posterior probability of the hypothesis being true given the portion of the signal data by combining a prior probability of the hypothesis and a conditional probability of observing the portion of the signal data given the hypothesis, wherein the conditional probability of observing the portion of the signal data given the hypothesis is determined based at least upon:
the parameterization of the portion of the signal data; and
the probability density function for at least one of the plurality of parameters;
using the posterior probability to determine that the hypothesis is true;
updating at least one of the probability density functions for the plurality of parameters using the parameterization of the portion of the signal data;
based on the hypothesis being true, using the parameterization of the portion of the signal data based upon the hypothesis for a further process, the further process comprising encoding the electrocardiogram signal for transmission; and
transmitting parameters corresponding to the electrocardiogram signal that has been encoded for transmission.

2. A method as claimed in claim 1, wherein updating at least one of the probability density functions for the plurality of parameters using the parameterization of the portion of the signal data comprises:
using a Bayesian framework to apply a likelihood to a prior probability density function to obtain a posterior probability.

3. A method as claimed in claim 1, wherein updating at least one of the probability density functions for the plurality of parameters using the parameterization of the portion of the signal data comprises: updating at least the probability density function for the parameter that positions the feature of interest within the signal data before determining the posterior probability of the hypothesis being true.

4. A method as claimed in claim 1, wherein updating at least one of the probability density functions for the plurality of parameters using the parameterization of the portion of the signal data comprises:
updating the probability density function for the parameter that positions the feature of interest within the signal data by performing a Bayesian update on a prior, the original probability density function for the parameter that positions the feature of interest within the electrocardiogram signal, using a likelihood determined by a limited search of the signal data to identify the feature of interest.

5. A method as claimed in claim 1, wherein updating at least one of the probability density functions for the plurality of parameters using the parameterization of the portion of the signal data comprises:

updating at least some of the probability density functions for the plurality of parameters after determining the posterior probability of the hypothesis being true.

6. A method as claimed in claim 1, further comprising:
parameterizing the signal based upon an analysis of amplitude variation over time wherein at least some parameters are determined based on amplitudes of putative waves in the electrocardiogram signal, and at least some parameters are based on inter-wave and intra-wave time durations for putative waves in the electrocardiogram signal.

7. A method as claimed in claim 1, wherein determining a posterior probability of the hypothesis being true given the portion of the signal data by combining a prior probability of the hypothesis and a conditional probability of observing the portion of the signal data given the hypothesis, comprises:
creating a product by multiplying the conditional probability of observing the portion of signal data given the hypothesis by the prior probability of the hypothesis.

8. A method as claimed in claim 7, further comprising:
normalizing the product by dividing by the sum of
a conditional probability of observing the portion of the signal data given the hypothesis multiplied by a prior probability of the hypothesis and
a probability of the portion of the signal data given a competing hypothesis multiplied by a prior probability of the competing hypothesis.

9. An apparatus comprising:
at least one processor; and
at least one memory storing instructions that, when executed by the at least one processor, cause the apparatus at least to perform:
obtaining evidence, based on an electrocardiogram signal from one or more sensors for the electrocardiogram signal for a subject's heart, the evidence including a probability density function for each of a plurality of parameters for parameterizing the electrocardiogram signal, including at least one probability density function for a parameter, of the plurality of parameters, that positions a recurrent feature of interest within signal data of the electrocardiogram signal, wherein the feature of interest is an R-peak of a PORST complex in the electrocardiogram signal;
parameterizing a portion of the signal data from the electrocardiogram signal based upon a hypothesis that a point of interest in the signal data is a position of the feature of interest;
determining a posterior probability of the hypothesis being true given the portion of the signal data by combining a prior probability of the hypothesis and a conditional probability of observing the portion of the signal data given the hypothesis,
wherein the conditional probability of observing the portion of the signal data given the hypothesis is determined based at least upon:
the parameterization of the portion of the signal data; and
the probability density function for at least one of the plurality of parameters;
using the posterior probability to determine that the hypothesis is true;
updating at least one of the probability density functions for the plurality of parameters using the parameterization of the portion of the signal data;
based on the hypothesis being true, using the parameterization of the portion of the signal data based upon the hypothesis for a further process, the further process comprising encoding the electrocardiogram signal for transmission; and
transmitting parameters corresponding to the electrocardiogram signal that has been encoded for transmission.

10. The apparatus as claimed in claim 9, wherein the at least one memory further stores instructions that, when executed by the at least one processor, cause the apparatus at least to perform: using one or more machine learning algorithms to identify anomalies in the electrocardiogram signal and warn the subject via an audible warning that an anomaly has been detected or that a threshold has been exceeded.

11. A non-transitory computer readable medium, having a computer program stored thereon that when run on a processor enables the processor to cause:
obtaining evidence, based on an electrocardiogram signal from one or more sensors for the electrocardiogram signal for a subject's heart, the evidence including a probability density function for each of a plurality of parameters for parameterizing the electrocardiogram signal, including at least one probability density function for a parameter, of the plurality of parameters, that positions a recurrent feature of interest within signal data of the electrocardiogram signal, wherein the feature of interest is an R-peak of a PORST complex in an electrocardiogram signal;
parameterizing a portion of the signal data from the electrocardiogram signal based upon a hypothesis that a point of interest in the signal data is a position of the recurrent feature of interest, wherein the parameterizing comprises parameterizing the portion of the signal data based upon expected parameters that characterize the recurrent feature of interest of the electrocardiogram signal;
determining a posterior probability of the hypothesis being true given the portion of the signal data by combining a prior probability of the hypothesis and a conditional probability of observing the portion of the signal data given the hypothesis, wherein the conditional probability of observing the portion of the signal data given the hypothesis is determined based at least upon:
the parameterization of the portion of the signal data; and
the probability density function for at least one of the plurality of parameters;
using the posterior probability to determine that the hypothesis is true;
updating at least one of the probability density functions for the plurality of parameters using the parameterization of the portion of the signal data;
based on the hypothesis being true, using the parameterization of the portion of the signal data based upon the hypothesis for a further process, the further process comprising encoding the electrocardiogram signal for transmission; and
transmitting parameters corresponding to the electrocardiogram signal that has been encoded for transmission.

* * * * *